(12) United States Patent
Sugiyama et al.

(10) Patent No.: US 11,024,416 B2
(45) Date of Patent: Jun. 1, 2021

(54) TOMOGRAPHIC IMAGE PROCESSING DEVICE, OPHTHALMIC DEVICE COMPRISING THE SAME AND NON-TRANSITORY COMPUTER-READABLE RECORDING MEDIUM STORING COMPUTER-READABLE INSTRUCTIONS FOR TOMOGRAPHIC IMAGE PROCESSING DEVICE

(71) Applicant: Tomey Corporation, Nagoya (JP)

(72) Inventors: Satoshi Sugiyama, Nagoya (JP);
Yuichiro Nakata, Nagoya (JP);
Nobuyori Aoki, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 105 days.

(21) Appl. No.: 16/411,524

(22) Filed: May 14, 2019

(65) Prior Publication Data
US 2019/0355466 A1    Nov. 21, 2019

(30) Foreign Application Priority Data
May 16, 2018   (JP) .............................. JP2018-094727

(51) Int. Cl.
*G16H 30/40* (2018.01)
*G06T 7/00* (2017.01)
*A61B 3/10* (2006.01)

(52) U.S. Cl.
CPC ............. *G16H 30/40* (2018.01); *A61B 3/102* (2013.01); *G06T 7/0012* (2013.01); *G06T 2207/10072* (2013.01); *G06T 2207/20081* (2013.01); *G06T 2207/30041* (2013.01)

(58) Field of Classification Search
CPC   G06T 2207/10072; G06T 2207/10101; G16H 30/40; A61B 3/102
See application file for complete search history.

(56) References Cited

U.S. PATENT DOCUMENTS

| | | | |
|---|---|---|---|
| 2012/0184845 A1* | 7/2012 | Ishikawa | A61B 3/102 600/425 |
| 2013/0188135 A1* | 7/2013 | Iwase | A61B 3/14 351/206 |
| 2016/0331224 A1* | 11/2016 | Uji | A61B 3/102 |

FOREIGN PATENT DOCUMENTS

| | | |
|---|---|---|
| EP | 2957219 A1 | 12/2015 |
| EP | 3278720 A1 | 2/2018 |
| JP | 2017-176842 A | 10/2017 |

* cited by examiner

*Primary Examiner* — John J Lee
(74) *Attorney, Agent, or Firm* — Shumaker, Loop & Kendrick, LLP (57) ABSTRACT

A tomographic image processing device that includes an input unit configured to input a tomographic image of a subject eye; a processor; and a memory storing computer-readable instructions therein. The computer-readable instructions, when executed by the processor, may cause the processor to execute: acquiring a tomographic image of a normal eye; acquiring a tomographic image of an eye having an abnormal portion; extracting a feature amount of the abnormal portion by using machine learning from the tomographic image of the normal eye and the tomographic image of the eye having the abnormal portion; acquiring a tomographic image of the subject eye inputted to the input unit; and determining whether the tomographic image of the subject eye includes an abnormal portion based on the feature amount.

8 Claims, 9 Drawing Sheets

FIG. 13

TOMOGRAPHIC IMAGE PROCESSING DEVICE, OPHTHALMIC DEVICE COMPRISING THE SAME AND NON-TRANSITORY COMPUTER-READABLE RECORDING MEDIUM STORING COMPUTER-READABLE INSTRUCTIONS FOR TOMOGRAPHIC IMAGE PROCESSING DEVICE

CROSS-REFERENCE

This application claims priority to Japanese Patent Application No. 2018-094727, filed on May 16, 2018, the entire contents of which are incorporated herein by reference.

TECHNICAL FIELD

The technique disclosed herein relates to a technique for processing a tomographic image of a subject eye.

BACKGROUND

An optical tomographic image capturing device configured to capture tomographic images of a subject eye has been developed. For example, an optical tomographic image capturing device of Japanese Patent Application Publication No. 2017-176842 is provided with a measurement optical system that provides light from a light source to inside of a subject eye and guides reflected light thereof, and a reference optical system that provides light from the light source to a reference surface and guides reflected light thereof. In measurement, positions of respective portions inside the subject eye are specified from interference light in which the reflected light guided by the measurement optical system is combined with the reflected light guided by the reference optical system. Then, tomographic images of the subject eye are generated from the specified positions of the respective portions of the subject eye.

SUMMARY

Tomographic images of a subject eye captured by the image capturing device described in Japanese Patent Application Publication No. 2017-176842 may be used for an examiner such as a doctor to diagnose a condition of the subject eye. In this case, the examiner observes the tomographic images of the subject eye for the diagnosis. However, since a number of the tomographic images of the subject eye captured by the image capturing device is enormous, there has been a problem that a burden on the examiner to observe all the tomographic images and to diagnose the subject eye accurately was excessively large. The disclosure herein discloses a technique that facilitates diagnosis when an examiner diagnoses a subject eye by using tomographic images of the subject eye.

A tomographic image processing device disclosed herein may comprise: an input unit to which a tomographic image of a subject eye is inputted; a processor; and a memory storing computer-readable instructions therein. The computer-readable instructions, when executed by the processor, may cause the processor to execute: acquiring a tomographic image of a normal eye; acquiring a tomographic image of an eye having an abnormal portion; extracting a feature amount of the abnormal portion by using machine learning from the tomographic image of the normal eye and the tomographic image of the eye having the abnormal portion; acquiring a tomographic image of the subject eye inputted to the input unit; and determining whether the tomographic image of the subject eye includes an abnormal portion based on the feature amount.

Another tomographic image processing device disclosed herein may comprise: an input unit to which a tomographic image of a subject eye is inputted; a processor; and a memory storing computer-readable instructions therein. The computer-readable instructions, when executed by the processor, may cause the processor to execute: acquiring an image for machine learning, the image for machine learning comprising a tomographic image of an eye with a line drawn between tissues in the tomographic image; extracting a feature amount of inter-tissue boundary by using the machine leaning from the image for the machine learning; acquiring a tomographic image of the subject eye inputted to the input unit; and determining an inter-tissue boundary in the tomographic image of the subject eye based on the feature amount.

An ophthalmic device disclosed herein may comprise: an image capturing unit configured to capture a tomographic image of a subject eye; and any one of the above tomographic image processing devices, the tomographic image processing device configured to process the tomographic image of the subject eye inputted from the image capturing unit.

Further, the disclosure herein discloses a computer program for realizing the tomographic image processing described above.

BRIEF DESCRIPTION OF DRAWINGS

FIGS. 7A and 7B are examples of tomographic images including a portion determined as an abnormal portion by the tomographic image processing device, where FIG. 7A is a tomographic image including the portion determined as an abnormal portion.

FIGS. 8A and 8B are other examples of tomographic images including a portion determined as an abnormal portion by the tomographic image processing device, where FIG. 8A is a tomographic image including the portion determined as an abnormal portion.

DETAILED DESCRIPTION

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved tomographic image processing devices, ophthalmic devices and non-transitory computer-readable recording mediums storing computer-readable instructions for a tomographic image processing device, as well as methods for using and manufacturing the same.

Moreover, combinations of features and steps disclosed in the following detailed description may not be necessary to practice the invention in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

A tomographic image processing device disclosed herein may comprise: an input unit to which a tomographic image of a subject eye is inputted; a processor; and a memory storing computer-readable instructions therein. The computer-readable instructions, when executed by the processor, may cause the processor to execute: acquiring a tomographic image of a normal eye; acquiring a tomographic image of an eye having an abnormal portion; extracting a feature amount of the abnormal portion by using machine learning from the tomographic image of the normal eye and the tomographic image of the eye having the abnormal portion; acquiring a tomographic image of the subject eye inputted to the input unit; and determining whether the tomographic image of the subject eye includes an abnormal portion based on the feature amount.

In the tomographic image processing device as above, the feature amount of the abnormal portion can be extracted by using the acquired tomographic image of the normal eye and the acquired tomographic image of the eye having the abnormal portion. Due to this, whether an abnormal portion is present or not can be determined based on the feature amount of the abnormal portion. Thus, an examiner simply needs to diagnose the determined abnormal portion and does not have to carefully observe every tomographic image of the subject eye. Due to this, a burden on the examiner in diagnosing the subject eye can be reduced, as well as it can be avoided that an abnormal portion is overlooked due to observation of an enormous number of tomographic images.

The tomographic image processing device disclosed herein may further comprise a display unit configured to display an image of the subject eye. When the display unit displays the tomographic image of the subject eye in a case where it is determined that the tomographic image of the subject eye includes the abnormal portion, the display unit may be configured to be capable of displaying the abnormal portion and a portion where the abnormal portion does not exist in different manners. According to such a configuration, the presence of the abnormal portion can be notified to the examiner by displaying the tomographic image of the subject eye that has been determined as including the abnormal portion on the display unit. Further, since the abnormal portion and the portion where the abnormal portion does not exist can be displayed in different manners, the examiner can easily recognize the abnormal portion.

In the tomographic image processing device disclosed herein, the tomographic image of the subject eye may comprise a first tomographic image and a second tomographic image, the first tomographic image being captured by irradiating the subject eye with a first polarized wave, the second tomographic image being captured by irradiating the subject eye with a second polarized wave that has a vibration direction different from the first polarized wave. The computer-readable instructions, when executed by the processor, may further cause the tomographic image processing device processor to execute: calculating an entropy based on the first tomographic image and the second tomographic image for a same cross section of the subject eye. According to such a configuration, the entropy (randomness) is calculated from the two tomographic images for the same cross section, by which a condition which is hard to detect by a single tomographic image, such as a condition of tissues in the subject eye, can be visualized. Due to this, the examiner can more accurately diagnose the subject eye.

Another tomographic image processing device disclosed herein may comprise: an input unit to which a tomographic image of a subject eye is inputted; a processor; and a memory storing computer-readable instructions therein. The computer-readable instructions, when executed by the processor, may cause the processor to execute: acquiring an image for machine learning, the image for machine learning comprising a tomographic image of an eye with a line drawn between tissues in the tomographic image; extracting a feature amount of inter-tissue boundary by using the machine leaning from the image for machine learning; acquiring a tomographic image of the subject eye inputted to the input unit; and determining an inter-tissue boundary in the tomographic image of the subject eye based on the feature amount.

In the tomographic image processing device as above, the feature amount of inter-tissue boundary can be extracted by using the image with the line drawn between tissues in the tomographic image as the image for machine learning. Due to this, the inter-tissue boundary in the tomographic image of the subject eye can be determined. Thus, the examiner does not have to determine the inter-tissue boundary for every tomographic image of the subject eye. Due to this, the work burden on the examiner can be reduced and the diagnosis of the subject eye can be facilitated.

The tomographic image processing device disclosed herein may further comprise a display unit configured to display an image of the subject eye. The display unit may be configured to display the image of the subject eye with a line that is drawn along the determined inter-tissue boundary superimposed over the image of the subject eye. According to such a configuration, the display unit can display the image of the subject eye with the line between tissues drawn thereon. Due to this, the examiner can easily identify the inter-tissue boundary in each tomographic image.

An ophthalmic device disclosed herein may comprise: an image capturing unit configured to capture a tomographic image of a subject eye; and any one of the above tomographic image processing devices, the tomographic image processing device configured to process the tomographic image of the subject eye inputted from the image capturing unit.

In the ophthalmic device as above, the tomographic image of the subject eye captured by the image capturing unit is inputted to the input unit comprised in any one of the above tomographic image processing devices. Due to this, effects similar to those of the tomographic image processing device can be achieved.

Further, the disclosure herein discloses a computer program for realizing the tomographic image processing as described above.

EMBODIMENTS

First Embodiment

Figure 1:
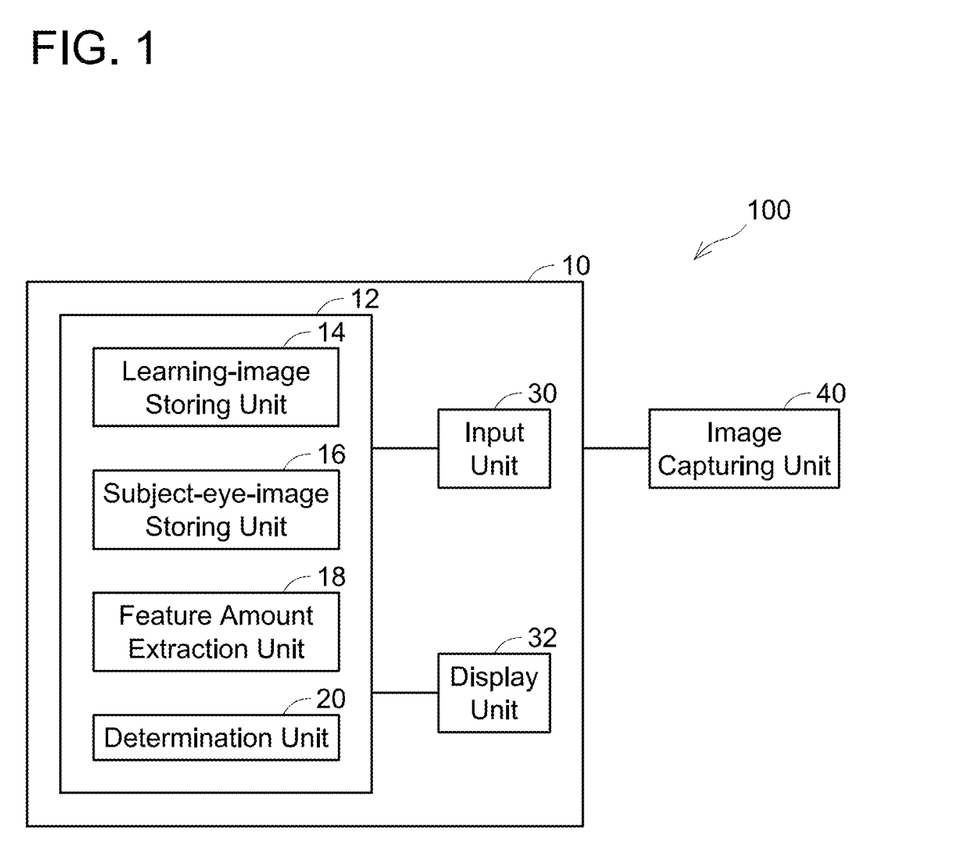
FIG. 1 is a diagram showing a schematic configuration of an ophthalmic device according to an embodiment.

Hereinbelow, an ophthalmic device 100 according to an embodiment will be described. As shown in FIG. 1, the ophthalmic device 100 includes a tomographic image processing device 10 and an image capturing unit 40. The image capturing unit 40 is configured to capture tomographic images of a subject eye by using Optical Coherence Tomography (OCT). In the image capturing unit 40, a type of OCT is not particularly limited so long as tomographic images of a subject eye can be captured. Further, since a configuration used in a publicly known ophthalmic device can be used as the image capturing unit 40, detailed descriptions thereof will be omitted.

The tomographic image processing device 10 includes a processor 12, an input unit 30, and a display unit 32. The processor 12 may be constituted of, for example, a computer provided with a CPU, a ROM, a RAM, and the like. The processor 12 functions as a feature amount extraction unit 18, a determination unit 20, and the like that are shown in FIG. 1, by the computer executing a program. Processes by the feature amount extraction unit 18 and the determination unit 20 will be described later in detail.

Further, as shown in FIG. 1, the processor 12 is provided with a learning-image storing unit 14 and a subject-eye-image storing unit 16. The learning-image storing unit 14 is configured to store tomographic images of eyes to be used in machine learning (hereinbelow, may simply be termed "machine-learning tomographic images"). For example, examples of the machine-learning tomographic images include a tomographic image of an eye in a normal condition, a tomographic image of an eye having an abnormal portion, and a tomographic image of an eye with a line drawn along a boundary between tissues in the tomographic image of the eye. The subject-eye-image storing unit 16 is configured to store tomographic images of the subject eye captured by the image capturing unit 40.

The input unit 30 is configured to input tomographic images of a subject eye captured by the image capturing unit 40. The input unit 30 is configured to input the tomographic images of the subject eye to the subject-eye-image storing unit 16. Further, the input unit 30 is configured to accept an input of machine-learning tomographic images. The input unit 30 is configured to input the machine-learning tomographic images to the learning-image storing unit 14.

The display unit 32 is configured to display a tomographic image of a subject eye. Further, on the display unit 32, the tomographic image of the subject eye is displayed with information determined by machine learning (such as a mark surrounding an abnormal portion, a line indicating an inter-tissue boundary, etc.) added thereon. The information determined by the machine learning will be described later in detail.

A process in which the tomographic image processing device 10 determines whether an abnormal portion is included in tomographic images of a subject eye will be described with reference to FIGS. 2 to 7. The process in which the tomographic image processing device 10 determines whether an abnormal portion is included in tomographic images of a subject eye includes a process in which the tomographic image processing device 10 extracts a feature amount of an abnormal portion by machine learning (see FIG. 2) and a process in which the tomographic image processing device 10 determines whether an abnormal portion is included in the tomographic images of the subject eye based on the feature amount extracted by the machine learning (see FIG. 6).

Figure 2:
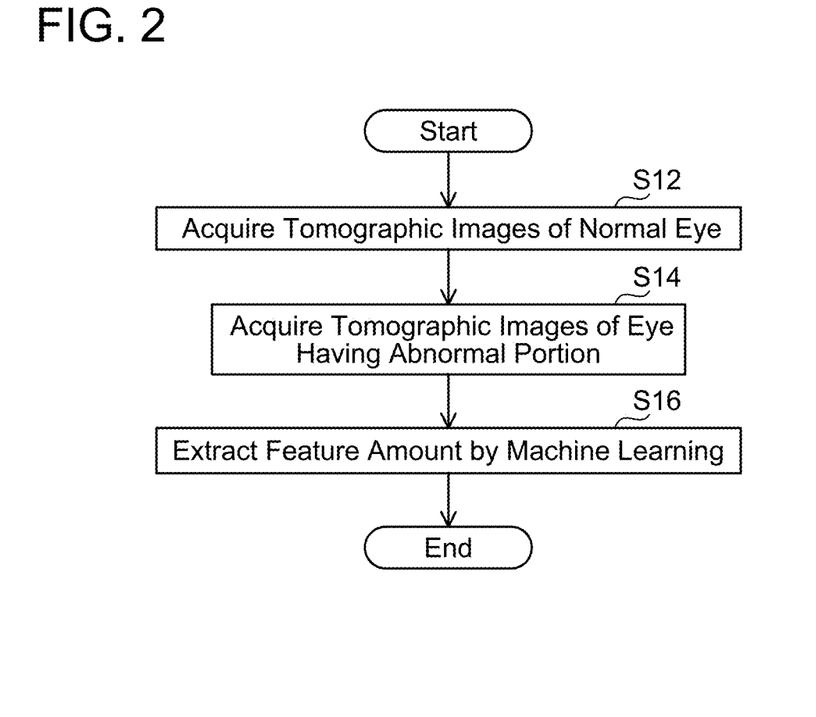
FIG. 2 is a flowchart showing an example of a process in which a tomographic image processing device extracts a feature amount of abnormal portion in tomographic images of eyes by machine learning.
Figure 3:
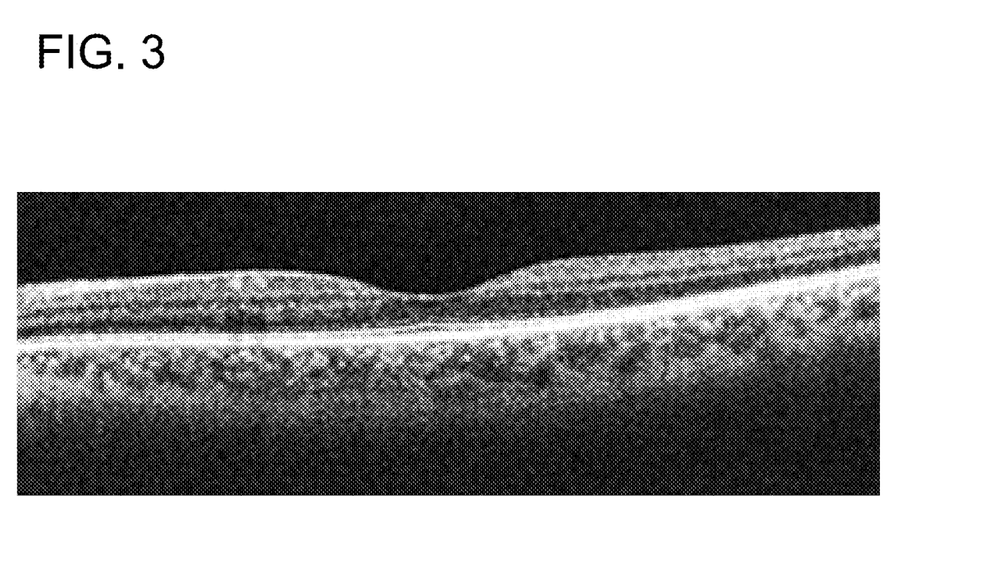
FIG. 3 is an example of a tomographic image of a normal eye, in which a normal macula is present.

Firstly, the process in which the tomographic image processing device 10 extracts a feature amount of an abnormal portion existing in tomographic images of eyes by the machine learning will be described with reference to FIGS. 2 to 5. As shown in FIG. 2, the processor 12 firstly acquires tomographic images of an eye in a normal condition (hereinbelow may be termed "normal eye") (S12). Specifically, an examiner inputs the tomographic images of the normal eye in the input unit 30. The tomographic images of the normal eye inputted herein may be all images for cross sections of one person's normal eye (for example, 256 tomographic images), or may be tomographic images of normal eyes of plural persons. The tomographic images of the normal eye include images having a feature profile, such as an image in which a normal macula is present (see FIG. 3). The tomographic images of the normal eye inputted to the input unit 30 are stored in the learning-image storing unit 14.

Figure 4:
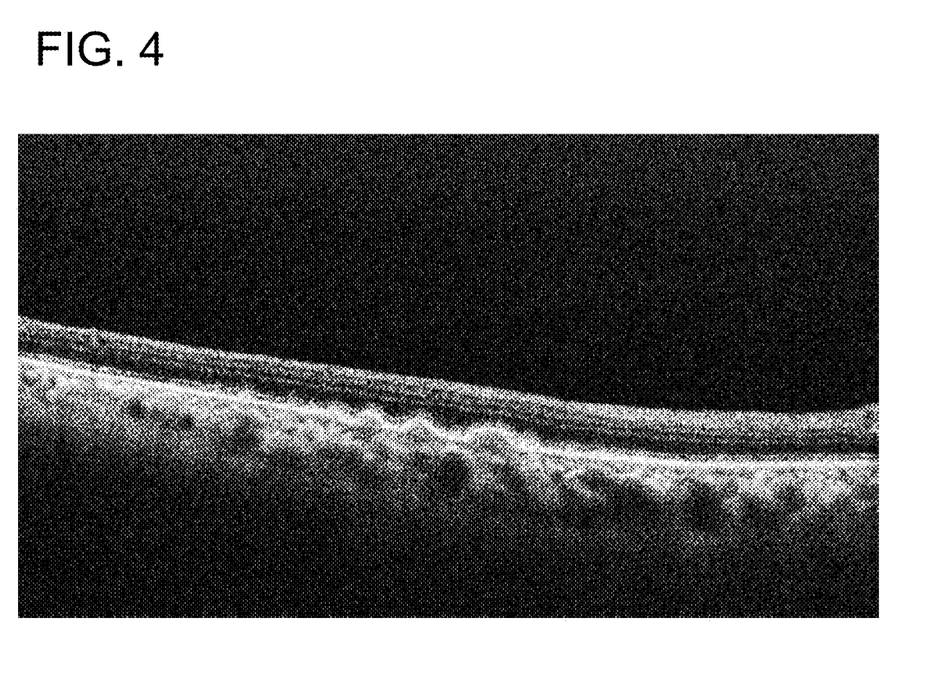
FIG. 4 is an example of a tomographic image of an eye having an abnormal portion, in which a macular degeneration is present.
Figure 5:
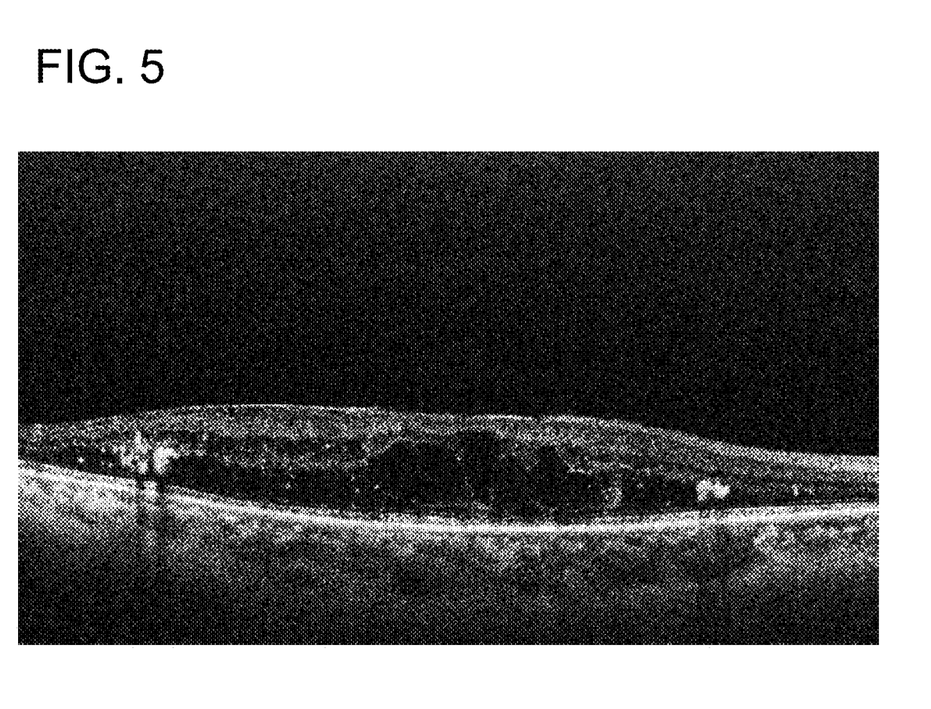
FIG. 5 is another example of a tomographic image of an eye having an abnormal portion, in which a retinal detachment is present.
Figure 7A:
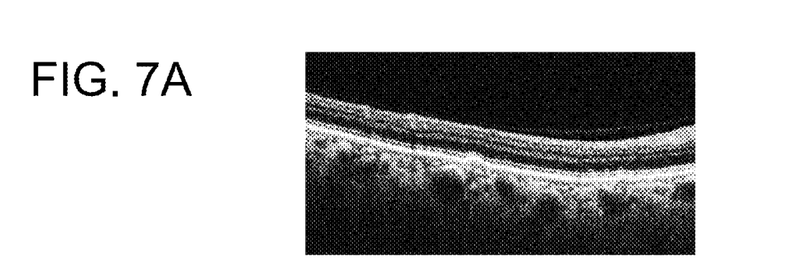

Next, the processor 12 acquires tomographic images of an eye having an abnormal portion (S14). Specifically, the examiner inputs the tomographic images of the eye having the abnormal portion to the input unit 30. The tomographic images of the eye having the abnormal portion may be, for example, tomographic images of the eye which have been determined as including the abnormal portion by the examiner such as a doctor. An abnormal portion includes not only a portion which has already been affected by an eye disease but also a precursor lesion which cannot be said as being affected by a disease yet. For example, the tomographic images of the eye having the abnormal portion include a tomographic image in which a macular degeneration is present as shown in FIG. 4, a tomographic image in which a retinal detachment is present as shown in FIG. 5, and further a tomographic image in which drusen, which is a precursor lesion, is present as shown in FIG. 7A. Upon inputting such tomographic images of eyes having abnormal portions, the examiner may input types of the abnormalities (such as the macular degeneration and the retinal detachment) present in the tomographic images along with the tomographic images. The tomographic images of the eye having the abnormal portion inputted to the input unit 30 are stored in the learning-image storing unit 14.

When the tomographic images of the normal eye and the tomographic images of the eye having the abnormal portion are acquired, the feature amount extraction unit 18 extracts a feature amount of the abnormal portion by using machine learning (S16). That is, the feature amount extraction unit 18 extracts the feature amount of the abnormal portion from the tomographic images of the normal eye and the tomographic images of the eye having the abnormal portion by the machine learning. A publicly known machine learning algorithm can be used as the machine learning of the present embodiment, thus the detailed description thereof will be omitted. The extracted feature amount of the abnormal portion is stored in a memory (not shown) provided in the processor 12.

Figure 6:
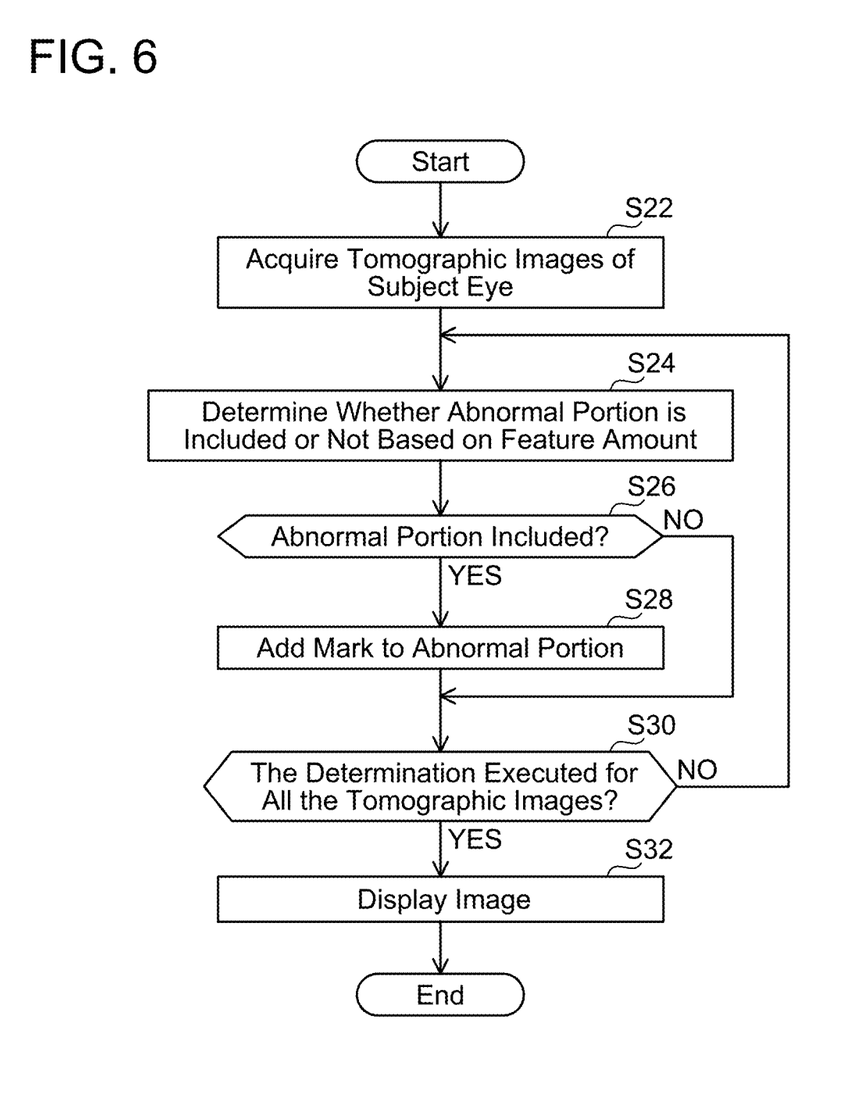
FIG. 6 is a flowchart showing an example of a process in which the tomographic image processing device determines whether an abnormal portion is included in tomographic images of a subject eye based on the feature amount extracted by machine learning.
Figure 7B:
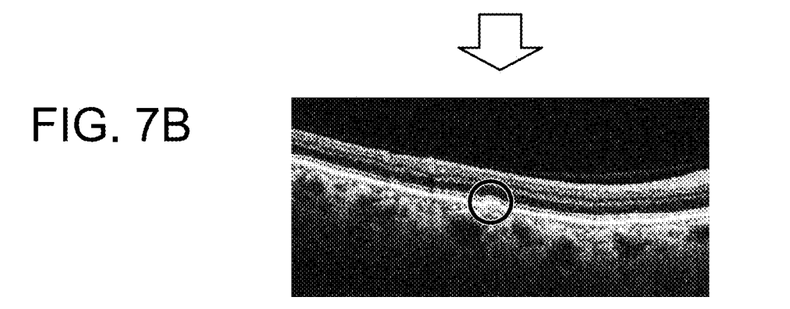
FIG. 7B is a tomographic image with a mark added at the portion determined as an abnormal portion.

Next, the process in which the tomographic image processing device 10 determines whether or not an abnormal portion is included in tomographic images of a subject eye based on the feature amount extracted by the machine learning will be described with reference to FIGS. 6 and 7. As shown in FIG. 6, the processor 12 firstly acquires tomographic images of a subject eye (S22). Specifically, the tomographic images of the subject eye are captured by the image capturing unit 40 and the captured tomographic images are inputted to the input unit 30. The tomographic images of the subject eye are images for respective cross sections of the subject eye, and for example, 256 images are captured. The tomographic images of the subject eye inputted to the input unit 30 are stored in the subject-eye-image storing unit 16.

When the tomographic images of the subject eye are acquired, the determination unit 20 determines whether or not an abnormal portion is included in the tomographic images of the subject eye based on the feature amount extracted in step S16 (S24). That is, one tomographic image is selected from among the inputted tomographic images of the subject eye and a determination is made on whether or not a portion having the extracted feature amount is included in the selected tomographic image. In a case where it is determined that an abnormal portion is included in step S24 (in a case of YES in step S26), the processor 12 adds a mark to the determined abnormal portion in the tomographic image of the subject eye (S28). For example, in the case where the determination unit 20 determines (specifies) there is a portion having the feature amount in step S24 as shown in FIG. 7A, the processor 12 adds a circular mark to surround the portion having the feature amount as shown in FIG. 7B. On the other hand, in a case where it is determined that an abnormal portion is not included in the tomographic image of the subject eye in step S24 (in a case of NO in step S26), the processor 12 skips step S28.

Next, the processor 12 determines whether or not the determination on the presence of an abnormal portion in step S24 has been executed for all the tomographic images of the subject eye acquired in step S22 (for example, for 256 images in the present embodiment) (S30). In a case where the determination on the presence of an abnormal portion has not been executed for all the tomographic images of the subject eye (in a case of NO in step S30), the processor 12 returns to step S24 and repeats the processes of steps S24 to S30. Due to this, the determination on whether or not an abnormal portion is included is made for all the tomographic images of the subject eye acquired in step S22.

On the other hand, in a case where the determination on the presence of an abnormal portion has been executed for all the tomographic images of the subject eye (in a case of YES in step S30), the processor 12 causes the display unit 32 to display the tomographic image of the subject eye (S32). At this occasion, if the mark was added in step S28 to an abnormal portion in the tomographic image of the subject eye to be displayed, the tomographic image of the subject eye is displayed with the mark added in step S28 superimposed thereon as shown in FIG. 7B, for example. Due to this, the portion which the tomographic image processing device 10 has determined as the abnormal portion can clearly be notified to the examiner. The examiner simply needs to diagnose the images including the portions indicated as the abnormal portions, thus does not need to carefully observe all the enormous number of tomographic images. As such, the diagnosis can be facilitated upon when the examiner diagnoses the subject eye by using the tomographic images of the subject eye.

In the present embodiment, the circular mark is added to a portion determined as having the feature amount to surround the portion, however, no limitation is placed on this configuration. A portion having the feature amount simply needs to be displayed in a different manner from other portions, and the portion having the feature amount may be displayed in a color different from that of the other portions, for example. Alternatively, the portion having the feature amount may be displayed in a blinking manner, or the portion having the feature amount may be displayed in an overlay display (see FIG. 8B).

Figure 8A:
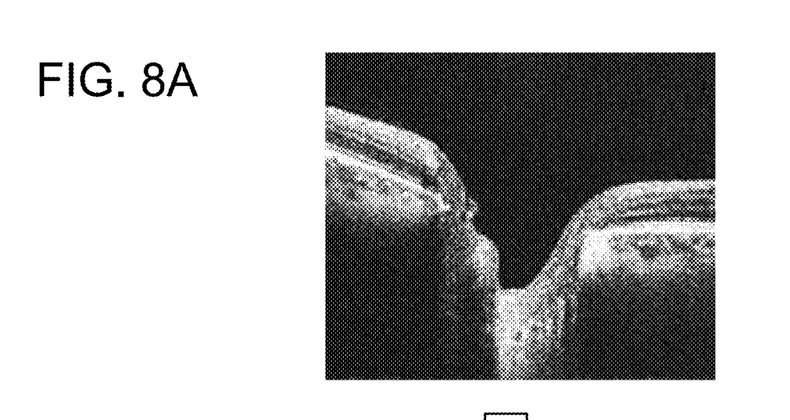
Figure 8B:
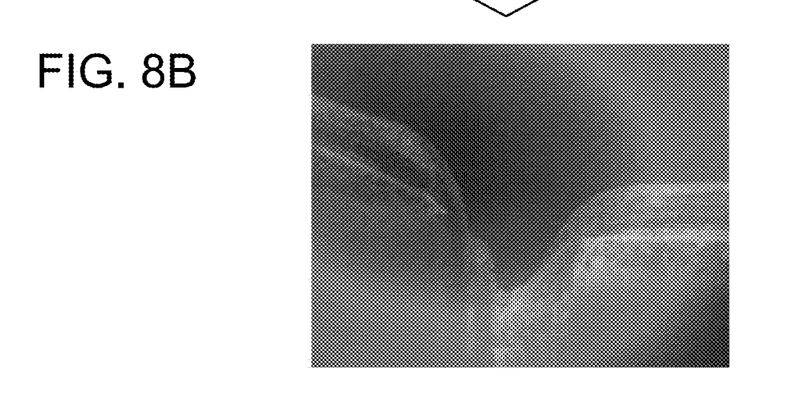
FIG. 8B is a tomographic image with an overlay display added at the portion determined as an abnormal portion.

In the present embodiment, the determination on whether or not the tomographic images of the subject eye include a portion having the feature amount of the abnormal portion is made based on the feature amount of the abnormal portion extracted by the machine learning. Thus, the determination can be made not only for a portion that has already been affected by a disease but also for a minor precursor lesion (drusen) which cannot be said as being affected by a disease yet, as shown in FIGS. 7A and 7B. Due to this, the examiner can more easily detect a minor lesion, which could have been overlooked without a careful observation, at an early stage. On the other hand, the use of machine learning could result in that a portion that is not affected by a disease or a lesion is determined as having the feature amount of the abnormal portion. For example, as shown in FIG. 8A, a portion indicating a normal optic disc could be determined as a depressed portion having the feature amount of the abnormal portion. Even in such a case, since this portion is displayed (in the overlay display in FIG. 8A) to the examiner as a portion having the feature amount of the abnormal portion, the examiner can diagnose whether the portion is an abnormality or not. That is, the tomographic image processing device 10 can notify the examiner of a portion which is suspected to be an abnormal portion. Due to this, portions which the examiner needs carefully diagnose can be narrowed down from among the enormous number of tomographic images, by which a burden on the examiner can be reduced.

The process in which the tomographic image processing device 10 extracts the feature amount of the abnormal portion by the machine learning may be executed continuously. By continuously executing the process of extracting the feature amount of the abnormal portion, reliability of the feature amount is increased and an accuracy for the process of determining whether an abnormal portion is present in the subject eye can further be improved. Further, for example, when the reliability of the extracted feature amount is sufficiently increased, the tomographic image processing device 10 may stop the process of extracting the feature amount of the abnormal portion by the machine learning. In the case where the process of extracting the feature amount of the abnormal portion is executed continuously, new images and/or the images determined in the process of determining whether an abnormal portion is present in the subject eye may be used as the machine-learning images. In a case where the images determined in the process of determining whether an abnormal portion is present in the subject eye are used as the machine-learning images, these images may be used by taking into account the determination result (diagnostic result) by the examiner.

As described above, in the present embodiment, the type of OCT employed in the image capturing unit 40 that captures the tomographic images of the subject eye is not particularly limited. For example, the image capturing unit 40 may employ a polarization-sensitive OCT to capture tomographic images of a subject eye. By using the polarization-sensitive OCT, tomographic images captured by irradiating the subject eye with a vertical wave and tomographic images captured by irradiating the subject eye with a horizontal wave can simultaneously be acquired. By using these two types of tomographic images, the processor 12 can calculate entropy, birefringent, and portion indicating blood flow in the tomographic images.

For example, an image indicating birefringent can be acquired by the following method. Firstly, a target portion (e.g., a retina) is captured by using the polarization-sensitive OCT. In doing so, speckles are generated by interference of scattered light caused by microstructures equal to or smaller than an OCT resolution. Phase difference of signals between polarized light of the generated speckles is displayed. Due to this, an image indicating birefringent is acquired. Further, an image indicating blood flow can be acquired by the following method. Firstly, a target portion (e.g., a retina) is captured plural times by using the polarization-sensitive OCT. In doing so, speckles are generated by interference of scattered light generated by microstructures equal to or smaller than the OCT resolution. Dispersion of scattering intensity signals or phase signals of the generated speckles is displayed. Due to this, an image indicating blood flow can be acquired.

For example, a condition (randomness) within tissues in the subject eye can be checked by displaying the calculated entropy. Further, by displaying an entropy calculated for each cross section of a retina as an en face image, how a substance, such as melanin, is distributed in the retina can be checked. Further, a condition of fibers in the retina can be checked by displaying the image indicating birefringent, and a blood flow flowing in the retina can be checked by displaying the image indicating blood flow. Such conditions within tissues are hard to grasp from tomographic images which simply capture positions of tissues in a subject eye (hereinbelow termed "regular tomographic images"). By observing both regular tomographic images of a subject eye and images thereof acquired by using the polarization-sensitive OCT (images indicating entropy, birefringent, or blood flow), the examiner can more accurately diagnose the subject eye. Due to this, the examiner can detect various types of diseases in the subject eye at an early stage.

Further, in each of cases of using the images indicating entropy in the tomographic images, of using the images indicating birefringent in the tomographic images, and of using the images indicating blood flow in the tomographic images, the machine learning is carried out by a method similar to the above-described method and a portion suspected as an abnormal portion is displayed to the examiner. In an example of using the images indicating entropy, the tomographic image processing device 10 extracts a feature amount of a abnormal portion by the machine learning and by using images indicating entropy of a normal eye and images indicating entropy of an eye having a abnormal portion. Then, whether or not a portion suspected as an abnormal portion is included in images indicating entropy of a subject eye is determined based on the extracted feature amount, a mark is added to the determined portion as described above, and the image is displayed. For the images indicating birefringent and for the images indicating blood flow, a feature amount of an abnormal portion is extracted by the machine learning in a similar method and whether a portion suspected to be an abnormal portion is included or not is determined based on the extracted feature amount. Due to this, a portion suspected to be an abnormal portion can be notified to the examiner with the images indicating entropy, with the images indicating birefringent, and with the images indicating blood flow.

In the diagnosis of a subject eye by the examiner, how the regular tomographic images, the images indicating entropy, the images indicating birefringent, and the images indicating blood flow of the subject eye are combined is not particularly limited. In a case with a combination of the regular tomographic images and the images indicating entropy of the subject eye, for example, a portion suspected to be an abnormal portion may be displayed to the examiner by the above-described method using the machine learning for the regular tomographic images of the subject eye, and the image indicating entropy may further be displayed for the displayed portion. That is, the tomographic image processing device 10 extracts a feature amount of an abnormal portion by the machine learning according to the above-described method and determines whether a portion suspected to be an abnormal portion is included in the regular tomographic images of the subject eye based on the extracted feature amount. Then, the examiner may further check the image indicating entropy for the portion corresponding to the determined portion in the regular tomographic images of the subject eye. Alternatively, a portion suspected to be an abnormal portion may be displayed to the examiner for the images indicating entropy by the above-described method using the machine learning, and the regular tomographic image (which has not been subjected to the machine learning) may further be displayed for the displayed portion. Alternatively, the tomographic image processing device 10 may determine whether a portion suspected to be an abnormal portion is included in the regular tomographic images of the subject eye based on the feature amount extracted by the machine learning as well as may determine whether a portion suspected to be an abnormal portion is included in the images indicating entropy of the subject eye based on the feature amount extracted by the machine learning. Similarly, the images indicating birefringent and the images indicating portion of blood flow may be combined in any combinations with the regular tomographic images and the images indicating entropy of the subject eye.

Second Embodiment

In the first embodiment, the determination on whether or not an abnormal portion is included in the tomographic images of the subject eye is made by using the machine learning, however, no limitation is placed on this configuration. For example, an inter-tissue boundary in tomographic images of a subject eye may be determined by using machine learning. Hereinbelow, a process of determining an inter-tissue boundary in tomographic images of a subject eye by using machine learning will be described with reference to FIGS. 9 to 13. The process in which the tomographic image processing device 10 determines an inter-tissue boundary in tomographic images of a subject eye includes a process in which a feature amount of inter-tissue boundary in tomographic images of eyes is extracted by machine learning (see FIG. 9) and a process in which the tomographic image processing device 10 determines an inter-tissue boundary in each of tomographic images of a subject eye based on the feature amount extracted by the machine learning (see FIG. 13).

Figure 9:
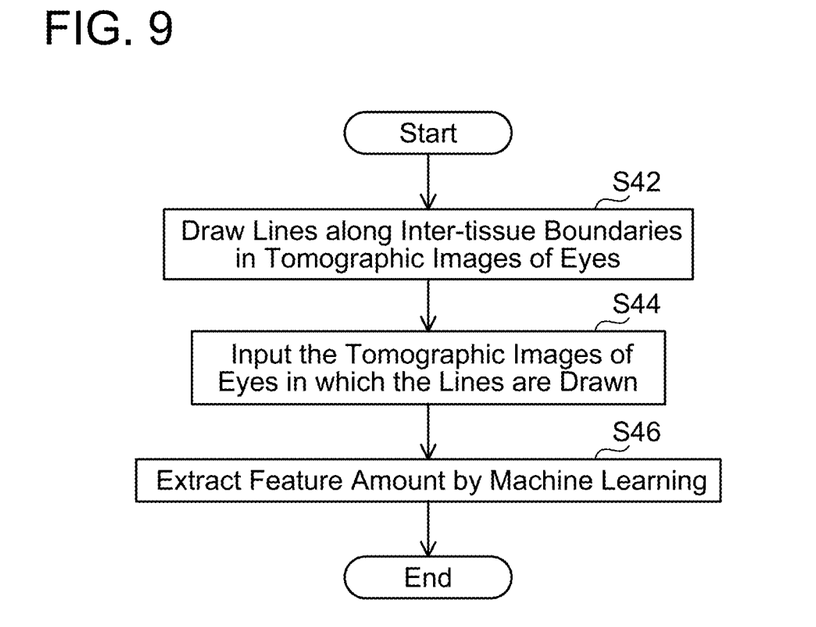
FIG. 9 is a flowchart showing an example of a process in which a feature amount of inter-tissue boundary in a tomographic image of an eye is extracted by machine learning.
Figure 10:
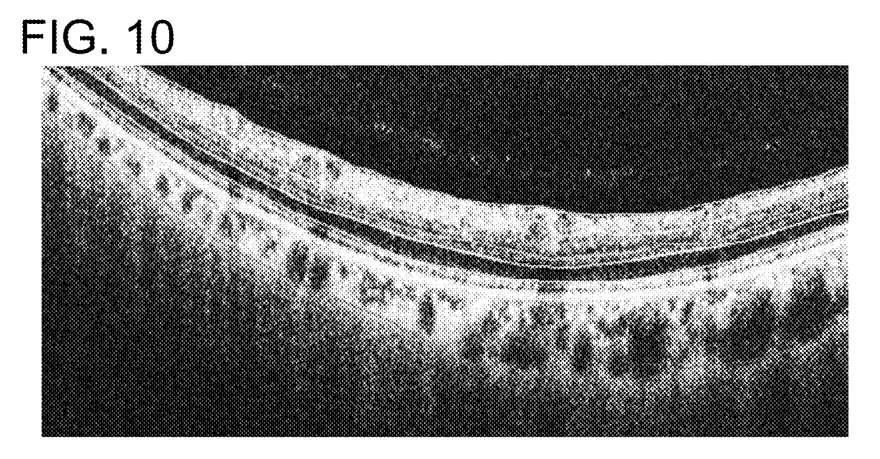
FIG. 10 is an example of a tomographic image of a normal eye (tomographic image in which a macula is present) in which a line is added to an inter-tissue boundary.
Figure 11:
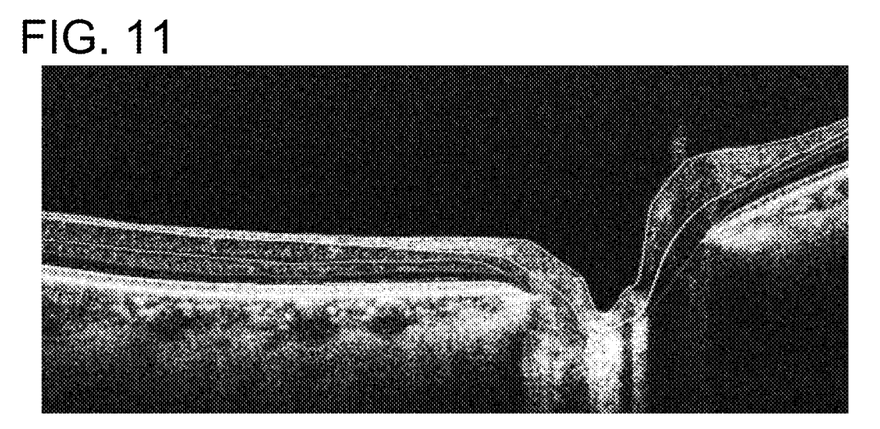
FIG. 11 is an example of a tomographic image of a normal eye (tomographic image in which an optic disc is present) in which a line is added to an inter-tissue boundary.
Figure 12:
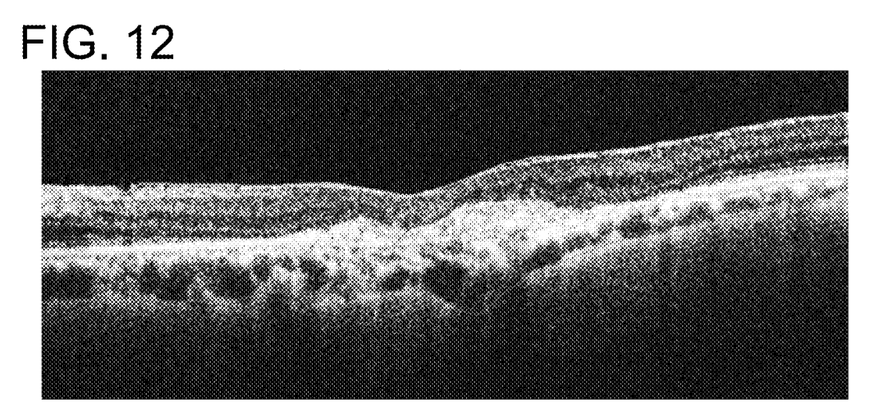
FIG. 12 is an example of a tomographic image including an abnormal portion in which a line is added to an inter-tissue boundary.

Firstly, the process of extracting a feature amount of inter-tissue boundary in tomographic images of eyes by the machine learning will be described with reference to FIGS. 9 to 12. As shown in FIG. 9, the examiner firstly adds a line to an inter-tissue boundary in each of tomographic images of an eye (S42). The tomographic images to which the lines have been added are the machine-learning tomographic images. Specifically, the examiner observes each tomographic image of the eye to determine an inter-tissue boundary therein. Then, the examiner manually adds a line to the determined boundary. For example, as shown in FIGS. 10 and 11, the examiner adds the lines to portions determined as inter-tissue boundaries in tomographic images of a normal eye. The tomographic images of the normal eye include images having a feature profile, such as a macula (see FIG. 10) and an optic disc (see FIG. 11). Further, the examiner also adds the lines to portions determined as inter-tissue boundaries in tomographic images of an eye having an abnormal portion. For example, as shown in FIG. 12, in the tomographic image of the eye having the abnormal portion, an inter-tissue boundary may be obscure and hard to determine. The examiner empirically determines the inter-tissue boundary therein and manually adds the line to the determined boundary.

Next, the examiner inputs the tomographic images of the eyes in which the lines were added to the inter-tissue boundaries in step S42 to the input unit 30 (S44). The tomographic images of the eyes inputted to the input unit 30 are stored in the learning-image storing unit 14.

When the tomographic images of the eyes in which the lines were added to the inter-tissue boundaries are inputted, the feature amount extraction unit 18 of the tomographic image processing device 10 extracts a feature amount of inter-tissue boundary by using the machine learning (S46). Since the process of step S46 is substantially same as the process of step S16 of the first embodiment, the detailed description thereof will be omitted. The extracted feature amount of inter-tissue boundary is stored in the memory (not shown) provided in the processor 12.

Figure 13:
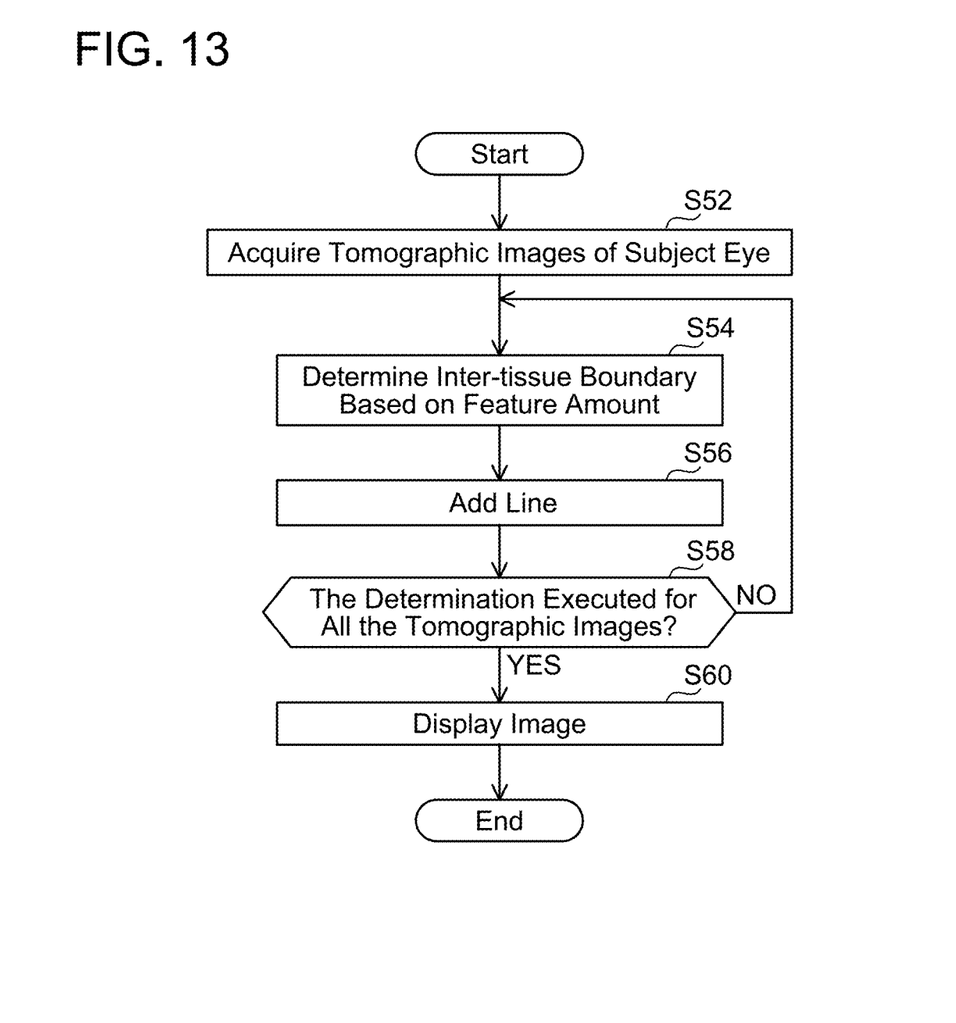
FIG. 13 is a flowchart showing an example of a process in which the tomographic image processing device determines an inter-tissue boundary in a tomographic image of the subject eye based on the feature amount extracted by machine learning.

Next, the process in which the tomographic image processing device 10 determines an inter-tissue boundary in each of tomographic images of a subject eye based on the feature amount extracted by the machine learning will be described with reference to FIG. 13. As shown in FIG. 13, the processor 12 firstly acquires tomographic images of a subject eye (S52). Since the process of step S52 is substantially same as the process of step S22 of the first embodiment, the detailed description thereof will be omitted.

When the tomographic images of the subject eye are acquired, the determination unit 20 determines an inter-tissue boundary in each of the tomographic images of the subject eye based on the feature amount extracted in step S46 (S54). As described above, an inter-tissue boundary may be hard to determine if an abnormal portion is included in the tomographic image of the subject eye (see FIG. 12). Further, an inter-tissue boundary may be hard to determine depending on image capturing conditions for the tomographic images. Even in such cases where inter-tissue boundaries are hard to determine, the determination unit 20 can determine inter-tissue boundaries since the feature amount has been extracted by the machine learning. When an inter-tissue boundary is determined, the processor 12 adds a line to this boundary portion (S56).

Next, the processor 12 determines whether or not the determination on inter-tissue boundary in step S54 has been executed for all the tomographic images of the subject eye (for example, 256 images in the present embodiment) (S58). In a case where the determination on inter-tissue boundary has not been executed for all the tomographic images of the subject eye (in a case of NO in step S58), the processor 12 returns to step S54 and repeats the processes of steps S54 to S58. On the other hand, in a case where the determination on inter-tissue boundary has been executed for all the tomographic images of the subject eye (in a case of YES in step S58), the processor 12 causes the display unit 32 to display the tomographic image of the subject eye (S60). At this occasion, on the display unit 32, the tomographic image of the subject eye is displayed with the line added in step S56 superimposed thereon.

In the present embodiment, the feature amount of inter-tissue boundary is extracted and the inter-tissue boundaries are determined in the tomographic images of the subject eye based thereon. Due to this, lines as shown in FIGS. 10 to 12 can be also added to the inter-tissue boundaries in the tomographic images of the subject eye. In doing so, even for the tomographic images in which the inter-tissue boundaries are hard to determine, the lines are automatically added to the inter-tissue boundaries based on the feature amount of inter-tissue boundary extracted by the machine learning. Due to this, the examiner does not need to determine the inter-tissue boundaries for all the tomographic images of the subject eye, by which the work burden on the examiner can be reduced.

In the present embodiment, the images for which the examiner had manually added the lines to the inter-tissue boundaries are used as the machine-learning images, however, no limitation is placed on this configuration. For example, tomographic images in which the lines were added to the inter-tissue boundaries by the tomographic image processing device 10 may be used as the machine-learning images. Due to this, a number of the machine-learning images can easily be increased.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. A tomographic image processing device comprising:
an input unit configured to input a tomographic image of a subject eye;
a processor; and
a memory storing computer-readable instructions therein, wherein
the computer-readable instructions, when executed by the processor, cause the processor to execute:
acquiring a tomographic image of a normal eye;
acquiring a tomographic image of an eye having an abnormal portion;
extracting a feature amount of the abnormal portion by using machine learning from the tomographic image of the normal eye and the tomographic image of the eye having the abnormal portion;
acquiring a tomographic image of the subject eye inputted by the input unit;
determining whether the tomographic image of the subject eye includes an abnormal portion based on the feature amount; and
a display unit configured to display an image of the subject eye, wherein when the display unit displays the tomographic image of the subject eye in a case where it is determined that the tomographic image of the subject eye includes the abnormal portion, the display unit is configured to display the abnormal portion and a portion where the abnormal portion does not exist in different manners.

2. The tomographic image processing device of claim 1, further comprising an image capturing unit configured to capture a tomographic image of a subject eye,
wherein the computer-readable instructions, when executed by the processor cause the processor to execute processing the tomographic image
of the subject eye inputted from the image capturing unit, and
the tomographic image processing device is an ophthalmic device.

3. A tomographic image processing device comprising:
an input unit configured to input a tomographic image of a subject eye;
a processor; and
a memory storing computer-readable instructions therein, wherein
the computer-readable instructions, when executed by the processor, cause the processor to execute:
acquiring a tomographic image of a normal eye;
acquiring a tomographic image of an eye having an abnormal portion;
extracting a feature amount of the abnormal portion by using machine learning from the tomographic image of the normal eye and the tomographic image of the eye having the abnormal portion;
acquiring a tomographic image of the subject eye inputted by the input unit;
determining whether the tomographic image of the subject eye includes an abnormal portion based on the feature amount;
wherein
the tomographic image of the subject eye comprises a first tomographic image and a second tomographic image, the first tomographic image being captured by irradiating the subject eye with a first polarized wave, the second tomographic image being captured by irradiating the subject eye with a second polarized wave that has a vibration direction different from the first polarized wave, and
the computer-readable instructions, when executed by the processor, further cause the processor to execute:
calculating an entropy based on the first tomographic image and the second tomographic image for a same cross section of the subject eye.

4. The tomographic image processing device of claim 3, further comprising an image capturing unit configured to capture a tomographic image of a subject eye,
wherein the computer-readable instructions, when executed by the processor, cause the processor to execute processing the tomographic image
of the subject eye inputted from the image capturing unit, and
the tomographic image processing device is an ophthalmic device.

5. A tomographic image processing device comprising:
an input unit configured to input a tomographic image of a subject eye;
a processor; and
a memory storing computer-readable instructions therein, wherein
the computer-readable instructions, when executed by the processor, cause the processor to execute:
acquiring a tomographic image of a normal eye;
acquiring a tomographic image of an eye having an abnormal portion;
extracting a feature amount of the abnormal portion by using machine learning from the tomographic image of the normal eye and the tomographic image of the eye having the abnormal portion;
acquiring a tomographic image of the subject eye inputted by the input unit;
determining whether the tomographic image of the subject eye includes an abnormal portion based on the feature amount;
wherein
the computer-readable instructions, when executed by the processor, further cause the processor to execute:
acquiring an image for machine learning, the image for machine learning comprising a tomographic image of an eye with a line drawn between tissues in the tomographic image;
extracting a feature amount of inter-tissue boundary by using the machine leaning from the image for the machine learning;
acquiring a tomographic image of the subject eye inputted by the input unit; and
determining an inter-tissue boundary in the tomographic image of the subject eye based on the feature amount.

6. The tomographic image processing device according to claim 5, further comprising a display unit configured to display an image of the subject eye,
wherein the display unit is configured to display the image of the subject eye with a line that is drawn along the determined inter-tissue boundary superimposed over the image of the subject eye.

7. The tomographic image processing device of claim 5, further comprising an image capturing unit configured to capture a tomographic image of a subject eye,
wherein the computer-readable instructions, when executed by the processor, cause the processor to execute processing the tomographic image
of the subject eye inputted from the image capturing unit, and the tomographic image processing device is an ophthalmic device.

8. A non-transitory computer-readable recording medium storing computer-readable instructions for a tomographic image processing device,
- wherein the computer-readable instructions, when executed by a processor of the tomographic image processing device, cause the processor to:
- acquire a tomographic image of a normal eye;
- acquire a tomographic image of an eye having an abnormal portion;
- extract a feature amount of the abnormal portion by using machine learning from the tomographic image of the normal eye and the tomographic image of the eye having the abnormal portion;
- acquire a tomographic image of a subject eye; and
- determine whether the tomographic image of the subject eye includes an abnormal portion based on the feature amount,
- wherein the computer-readable instructions, when executed by a processor of the tomographic image processing device, further cause the processor to:
- acquire an image for machine learning, the image for machine learning comprising a tomographic image of an eye with a line drawn between tissues in the tomographic image;
- extract a feature amount of inter-tissue boundary by using the machine learning from the image for the machine learning;
- acquire a tomographic image of a subject eye; and
- determine an inter-tissue boundary in the tomographic image of the subject eye based on the feature amount.

* * * * *